(12) United States Patent
Weisenthal

(10) Patent No.: US 8,278,033 B2
(45) Date of Patent: *Oct. 2, 2012

(54) EFFICIENT WELL BEING ASSESSMENT AND IMPROVED TREATMENT PROTOCOL

(76) Inventor: Larry Mark Weisenthal, Huntington Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/994,105

(22) PCT Filed: May 22, 2009

(86) PCT No.: PCT/US2009/045062
§ 371 (c)(1),
(2), (4) Date: Mar. 28, 2011

(87) PCT Pub. No.: WO2009/143478
PCT Pub. Date: Nov. 26, 2009

(65) Prior Publication Data
US 2011/0171214 A1      Jul. 14, 2011

Related U.S. Application Data

(60) Provisional application No. 61/055,413, filed on May 22, 2008.

(51) Int. Cl.
*G01N 33/53* (2006.01)
(52) U.S. Cl. ............................................ 435/4; 436/518
(58) Field of Classification Search ........................ None
See application file for complete search history.

(56) References Cited

U.S. PATENT DOCUMENTS

| | | |
|---|---|---|
| 2005/0266067 A1 | 12/2005 | Sengupta et al. |
| 2006/0199231 A1 | 9/2006 | Moore et al. |
| 2007/0190648 A1 | 8/2007 | Weisenthal |

FOREIGN PATENT DOCUMENTS

WO      WO-2007/075440      7/2007

OTHER PUBLICATIONS

Kimura et al. (PlosOne 2011, vol. 6, p. 1-11).*
Boos et al., J. Am. Col. Cardiol. (2006) 48:1538-1547.
Eichbaum, Anticancer Drugs (2005) 16:199-200.
International Search Report for PCT/US09/045062, mailed on Sep. 2, 2009, 3 pages.
International Preliminary Report on Patentability for PCT/US09/045062, issued Nov. 23, 2010, 6 pages.
Weisenthal et al., Cancer Research (1983) 43:749-757.

* cited by examiner

*Primary Examiner* — Jacob Cheu
(74) *Attorney, Agent, or Firm* — Morrison & Foerster LLP

(57) ABSTRACT

Methods to appraise general health and to assess the effectiveness of therapeutic agents are disclosed. These methods can be performed on blood samples or other bodily fluids and comprise effecting cell death of endothelial cells, staining the dead cells and observing them microscopically. In addition, the invention is directed to combination treatments for neoplastic diseases or other conditions characterized by unwanted angiogenesis by administering an antiangiogenesis agent while maintaining nontoxic levels of ethanol and/or DMSO in the blood.

17 Claims, 6 Drawing Sheets

A B

A B

EFFICIENT WELL BEING ASSESSMENT AND IMPROVED TREATMENT PROTOCOL

TECHNICAL FIELD

The invention relates to diagnostic tests useful in evaluative screening of subjects for general wellbeing. More particularly, the invention is directed to an inexpensive and convenient assay for circulating endothelial cells and for detection of endothelial cells in general. In addition, the invention relates to an improved protocol for treatment of conditions characterized by unwanted neovasculature, including neoplastic conditions.

BACKGROUND ART

It is generally recognized that circulating microvascular (endothelial) cells are important markers for a variety of disease states such as cardiac disease, cardiovascular disease and diabetes (Bos, C. J., et al., *J. Am. Col. Cardiol.* (2006) 48:1538-1547). Detecting such cells in the circulatory system is, however, problematic because of interference from other cells, such as platelets. Methods that involve separation of cells by type, or antibody labeling such as the use of antibodies directed to CD31, require time-consuming steps and often require expensive equipment.

PCT application US 2006/047954, published as WO 2007/075440 and incorporated herein by reference, which describes the work of the applicant herein, discloses a method for assessing the effect of drugs used in antineoplastic therapy in microaggregates of tumor biopsies by first identifying, through labeling with CD31 or through experienced observation, endothelial cells as opposed to neoplastic cells in the sample. The sample, after being subjected to a candidate drug, is stained with a dye which is taken up by dead cells but excluded by viable cells and then counterstained with a dye that is accepted by viable cells. When the sample is examined under a microscope for the particular dye combination selected, the blue/green dye which is excluded by viable cells shows the dead cells as "blueberries" in a background pink "pancake" of viable cells stained with the counterstain. It is possible, therefore, by virtue of the knowledge of which cells are cancer cells and which cells are endothelial cells to determine whether a given drug affects the cancer cells, endothelial cells or both. In general, it is shown that drugs known to inhibit angiogenesis, such as Avastin® (bevacizumab), result in the endothelial cells showing up dead in this assay while the tumor cells remain unaffected. Direct antineoplastic drugs result in the death of the tumor cells themselves, rather than the endothelial cells.

It has now been found that endothelial cells, when caused to become non-viable, not only absorb dyes excluded by viable cells, but also have a distinctive appearance which makes them recognizable even in the presence of other dead cells. Thus, it becomes practical to assess a heterogeneous sample, such as blood plasma, or a disaggregated form or extract of the microaggregates described in WO 2007/075440, for the presence of endothelial cells by subjecting the sample to an agent known to kill endothelial cells and staining with a suitable dye that renders the dead endothelial cells instantly recognizable under a microscope even to an unpracticed eye. This permits a rapid and efficient test for circulating endothelial cells wherein an elevated level of such cells is indicative of traumatic conditions in the subject.

It has also been found, surprisingly, that the nontoxic solvents DMSO and ethanol have themselves antiangiogenic effects and are able to lower the levels of vascular endothelial growth factor (VEGF) in cell cultures.

DISCLOSURE OF THE INVENTION

In one aspect, the invention is directed to a method to detect and quantify circulating endothelial cells in human or other vertebrate subjects which comprises subjecting a sample of a bodily fluid to an agent that is toxic to endothelial cells, followed by treating the sample with a dye excluded by viable cells but taken up by non-viable cells, and examining the sample under a microscope to detect, and, if desired, count the readily identifiable endothelial cells in the sample. Increased counts of endothelial cells in the circulatory system of the subject are indicators of a variety of conditions such as diabetes, cardiovascular problems and the like, as well as trauma such as muscular strain and bruising.

Thus, in this aspect, the invention is directed to a method to detect and optionally quantify circulating endothelial cells in a vertebrate subject which method comprises (a) contacting a bodily fluid obtained from a subject to be tested with an agent that is cytotoxic to endothelial cells;

(b) treating the cells with a dye that is excluded by viable cells but taken up by dead cells;

(c) observing the resulting cells under a microscope, and (d) identifying the endothelial cells in said culture by their small size, angular appearance and intense color.

Bodily fluids that are useable include blood, plasma and lymph.

If desired, the number of endothelial cells may be counted and the concentration of endothelial cells in the circulatory system calculated. The method may also include counterstaining with a stain taken up by viable cells.

The above method can be used to assess the effectiveness of therapeutic agents by evaluating the effect of the agents administered to the subject on the number of endothelial cells in the circulation of the subject tested. Animal models are particularly useful in this aspect of the invention, though effectiveness of treatments in human or veterinary patients can be evaluated as well.

It has also been found that because of the distinctive nature of the endothelial cells when treated as described herein, the method of the invention can be used to assess endothelial cells in tumors by disaggregating the required microaggregates described in the above-cited PCT publication and evaluating the disaggregated or extracted form for the quantity or presence of such cells.

In addition, the assay method of the invention has revealed that, surprisingly, the nontoxic substances DMSO and ethanol can potentiate the effects of antiangiogenesis drugs, since they themselves can exhibit this effect. Thus, in another aspect, the invention is directed to an improved method to treat conditions characterized by unwanted neovasculature which comprises administering to a subject in need of such treatment an antiangiogenic agent while maintaining blood levels of ethanol and/or DMSO that are nontoxic, but are sufficient to enhance the antiangiogenic effect of the primary drug.

BRIEF DESCRIPTION OF THE DRAWINGS

FIG. 1A shows the results of staining a suspension culture with Fast Green, counterstaining with hematoxylineosin (H&E) and then counterstaining with anti-CD31. FIG. 1B shows cells stained only with Fast Green/H&E. FIG. 1C shows the cultured cells treated with bevacizumab and then stained said Fast Green/H&E.

MODES OF CARRYING OUT THE INVENTION

Figure 1:
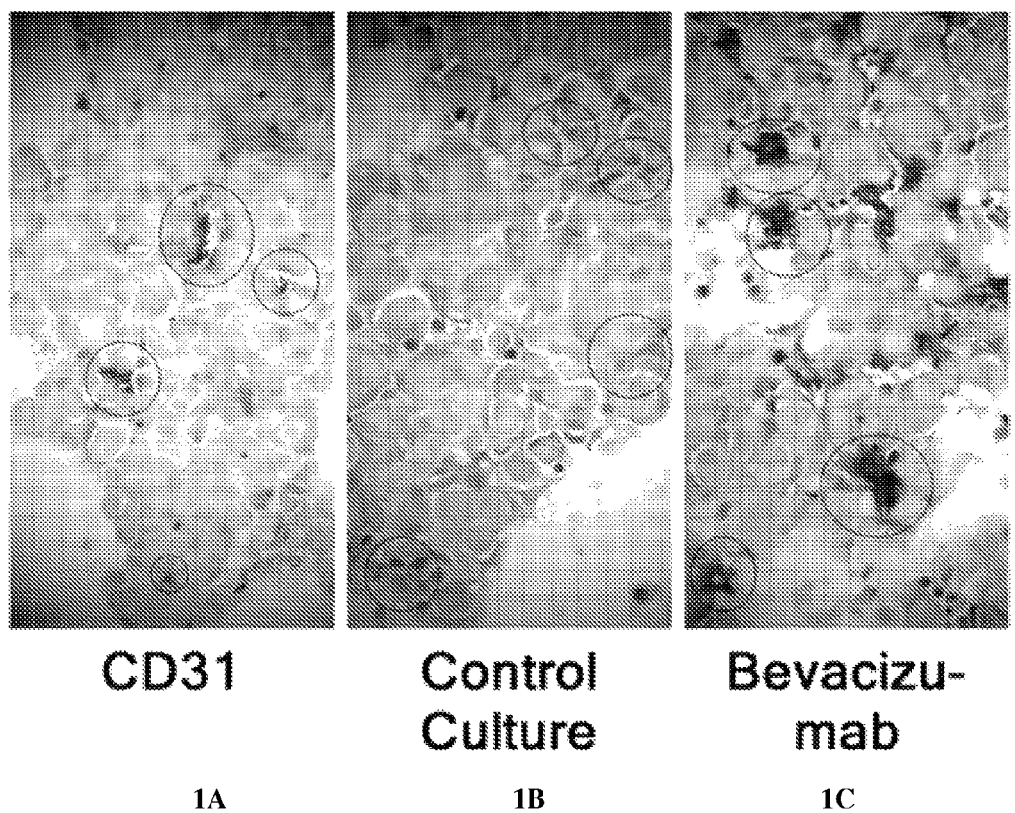
FIGS. 1A-1C show the effect of staining of endothelial cells selectively according to the invention method in comparison with CD31 staining.

The invention provides a useful diagnostic tool to assess the general physical condition of a subject and to assess the presence of traumatic effects of, for example, sports injuries or overactivity.

In the context of a general routine physical checkup of a normal subject, a finding of normal levels of circulating endothelial cells could spare the subject from additional tests in view of the known association of high counts of endothelial cells with conditions such as diabetes and cardiovascular problems. Tests designed to detect such conditions would not be, strictly speaking, necessary in the face of normal endothelial cell counts.

On the other hand, a finding of abnormally high endothelial circulating cells would indicate the need for further assessment. The availability of a simple test based on a small blood sample might be attractive in encouraging individuals to evaluate their overall health and such tests could be conducted, not only in single doctor's offices, but also in convenient locations now served by nurse practitioners or other paramedical professionals in drug stores and the like.

The method of the invention requires only simple equipment and minimal training of personnel to evaluate. This is true because the dead endothelial cells which are able to take-up dyes excluded from viable cells have distinctive appearances. They stain very heavily, they are angular, and they are smaller than contaminating cells. They are roughly one-third the size of lymphocytes.

While direct observation of the cells and scoring by eye is effective, the method lends itself to quantitation by instrumentation as well. Illustrated below, is the use of ImageJ software to quantitate the results of the assay.

As used herein, "antiangiogenic agent" or "antiangiogenesis agent" "anti-neovasculature" or "antimicrovascular agent" or "agent cytotoxic to endothelial cells" are used interchangeably to denote agents that are able to kill endothelial cells and thus decrease neovascularization. These agents may interact with VEGF, with VEGF receptors, or with other factors that are necessary to promote angiogenesis.

In general, such agents are useful in treating conditions that are characterized by unwanted neovasculature. These include cancers, macular degeneration and other conditions such as benign hypertrophies.

In the assay of the invention, a blood sample is optionally subjected to centrifugation, gravity sedimentation, differential cell lysis or other technique to remove the red blood cells (although, strictly speaking, this is unnecessary) and the resulting plasma treated with an agent known to be cytotoxic to endothelial cells, such as antibodies directed against vascular endothelial growth factor (VEGF) or other antiangiogenic agent. A convenient choice is Avastin® which is available commercially.

After treatment with the antiangiogenesis agent, the sample is treated with a suitable dye specific for non-viable cells, such as fast green. The method of the invention is not limited to these particular dyes. Any dyes with these features can be used.

The cells are then spun down to a microscope slide and evaluated.

If desired, the cells on the microscope slide may counterstained with, for example, Wright-Giemsa, H&E or other suitable stain. It is not necessary to use these particular dyes, but they are convenient embodiments.

The foregoing process is applicable not only to body fluids, but also to extracts of, or disaggregated forms of, microaggregate samples obtained from tumors as described in PCT publication WO 2007/075440. The neovasculature of the microaggregates appears to provide a scaffolding for retaining the three-dimensional structure of the microaggregates, and thus, one method for disaggregation is treatment with antiangiogenesis agents such as bevacizumab. When the scaffold is destroyed, free endothelial cells are released into the culture medium. The foregoing methods can be applied to assess the presence and/or amount of said cells then released.

This method can also be used to assess the effects of intended therapies on the endothelial cell population by treating a tissue sample, such as the microaggregate of the above-mentioned PCT publication, with the treatment to be tested and disaggregating the tissue sample or extracting the cells therefrom, and assessing the effect of the treatment on the endothelial cell population. In this case, the extract or disaggregation should not, itself, kill the endothelial cells. The dead endothelial cells can be detected and, if desired, counted as described above by treating them with a dye that is excluded by viable cells but taken up by dead cells and observing the resulting cells under a microscope. The dead endothelial cells are recognized by their small size, often angular appearance and often intense and refractile color.

It has also been found that both ethanol and DMSO are able to exert antiangiogenesis effects and are cytotoxic to endothelial cells. They can be used in combination with a primary drug that is an antiangiogenesis agent because they are non-toxic when used in low amounts. Thus, in addition to primary therapy with one or more antiangiogenesis drugs, a subject may be treated so as to maintain nontoxic levels of alcohol or DMSO in the blood. DMSO would be administered by, for example, IV injection, while blood alcohol levels can conveniently be maintained by administering alcohol orally in the form of conventional alcoholic beverages. Breathalyzer tests may be used to ensure that the appropriate alcohol levels are maintained during treatment. As noted in Example 6, below, a patient at the University of Pennsylvania was successfully treated with a combination of antiangiogenic agents and red wine. In addition, there is anecdotal evidence from the University of Heidelberg where a breast cancer patient with daily wine consumption of 1.5 l showed a 5-year+ remission on therapy with the antiangiogenic agent trastuzumab. This is reported by Eichbaum, M. H. R., *Anticancer Drugs* (2005) 16:199-200. It should be noted that this does not represent the combination therapy of the invention as the patient is a chronic alcoholic and not administered a controlled protocol.

Preparation A

In the Examples below, where cell culture methods derived from biopsies were used to conduct the experimental procedures, they were prepared as follows. The preparation is essentially as set forth in the above-referenced PCT publication WO 2007/075440.

Fresh biopsies or fluid aspirates are obtained from patients with cancer or other illnesses or from normal donors.

Specimens are typically submitted for conduct of the invention method via the anatomic pathology laboratories of the submitting hospitals, or, in some cases, directly from the operating room or a surgeon/physician office. Solid tumor specimens (not exposed to fixatives or frozen) are placed in cold transport medium ($CO_2$-independent medium, InvitroGen/GIBCO, Grand Island, N.Y., supplemented with penicillin/streptomycin, amphotericin B, insulin/selenium/transferrin, and 10% low endotoxin, heat inactivated fetal bovine serum). Specimens are then placed in sturdy Styrofoam® shipping boxes, containing 350 gm blocks of "blue ice" frozen to minus 20 degrees Celsius. These are then shipped either by a priority overnight delivery service or via local land courier. Fluid specimens are mixed well to suspend cell clusters and then poured into sterile 500 ml polypropylene transport bottles. Ten to fifteen units of heparin sulfate are added per ml of fluid submitted.

Copies of the official histopathology reports from the submitting hospitals should be received.

Solid tumors are minced to pieces smaller than 1 mm (small enough to be aspirated into a standard disposable 10 ml pipette) with high quality curved surgical scissors. Medium in which said tumors may have been transported is reserved, along with the supernatant from the tissue mince. Scissor-minced tumor pieces are digested with collagenase/DNase in RPMI-1640 containing antibiotics and 10% fetal calf serum. Specimens are digested in 50 ml disposable polypropylene centrifuge tubes, assisted by gentle mixing with plastic-coated, magnetic stirring bars over a stirring plate. Specimens are thusly mixed until complete gross digestion has taken place—typically about 2-3 hours for a 1-3 gram specimen. Cytospin slides are then prepared from all cell fractions (transport medium, supernatant from tissue mince, and enzyme digestate), and stained with fast green-H&E, as described previously (Weisenthal, et al., "A Novel Dye Exclusion Method for Testing in vitro Chemosensitivity of Human Tumors," *Cancer Res*. (1983) 43:749-757).

Fluid specimens are centrifuged in their entirety to collect all cells in the specimen. Cells are then resuspended in the above RPMI-1640-based medium and cytospins are prepared as described above.

To normalize the results, "day zero" slides are prepared, depicting the condition of the cells not exposed to treatment at the beginning of the assays, and "end culture" slides of negative control (non-exposed cells) are also prepared.

To assay for endothelial cells are mixed with, for example, 10% (volume/volume) or, for example, 1% (volume/volume) or intermediate percentages of antiangiogenic drug containing solution or vehicle control (most typically 0.9% NaCl). Final volume of cell suspension/drug solution (or vehicle) plated for culture can be 0.12 ml. Culturing is in polypropylene round bottom, 96-well culture dishes in a humidified 37° C. incubator for a standardized duration of time.

Stock solutions are generally prepared at ten times-100 times the desired concentrations, aliquotted into single-use, 0.5 ml conical polypropylene tubes, and frozen at −70° C. prior to use. Some drugs are maintained at refrigerator temperature, according to manufacturer's recommendations.

Cells are cultured with the index concentration of each drug and, if desired, with dilutions of the index concentration, where the index concentration is determined from training set assays or from the literature. Negative controls generally consist of 0.9% NaCl, and/or the vehicle in which an antiangiogenic drug is dissolved. Replicate 96-well plates are tested.

In addition, details of tumor cell isolation, cell culture conditions, slide preparation and staining are described at the website of Weisenthal.org.

The following examples are offered to illustrate but not to limit the invention.

EXAMPLE 1

Detection of Endothelial Cells

Using the procedures set forth in Preparation A, a pancreatic carcinoid tumor was visualized after 96 hours in suspension culture in the presence and absence of 2.5 mg/ml bevacizumab. The cultures were stained with the above-described Fast Green/H&E stain/counterstain. FIG. 1B shows the results in a control culture that has not been treated with bevacizumab. It is apparent that the endothelial cells are barely visible. FIG. 1A shows the results of the control culture (not treated with bevacizumab) when CD31 staining is used to identify the endothelial cells. Again, they are not particularly conspicuous. FIG. 1C shows the results when the culture has been treated with bevacizumab, resulting in endothelial cell death. The appearance of the endothelial cells is quite striking. The characteristic "blueberry pancake" appearance described in the above-referenced WO 2007/075440 publication is observed.

EXAMPLE 2

Comparison of Various Chemotherapeutic Agents

The cultures of Example 1 were treated with various candidate chemotherapeutic drugs in comparison to bevacizumab at 2.5 mg/ml and stained as described in Example 1. The various drugs were rated by scoring on a 0+ to 5+ scale for the anti-microvascular effects, with 5+ being the highest possible score. As shown in FIGS. 2A-2H, gefitinib scored only 0; sunitinib scored 1+, sorafenib scored 3+ and both erlotinib and bevacizumab scored 4+. The "nib" drugs are kinase inhibiting drugs.

Further results are tabulated in Table 1 where slides were scored for anti-microvascular effects as described above and also for direct antitumor effects as described on the Weisenthal.org website. For this determination, the results provided in Table 1 are 10× multiples of the scoring system of the previous paragraph. The table also shows the concentration of each drug employed. Bevacizumab was dispensed both in a vehicle containing 0.9% NaCl and in a vehicle which resulted in a final concentration in the culture medium of 0.5% DMSO/0.5% ethanol. Gefitinib and sunitinib were dispensed in 0.9% NaCl, but erlotinib, sorafenib, and imatinib were dispensed to provide the final 0.5% DMSO/0.5% ethanol concentration.

TABLE 1

|  | N paired comparisons | Anti-Vascular Score (AVS) (Avg) | Vehicle Anti-Vascular Score (VAVS) (Avg) | P2 (paired comparison AVS vs VAVS) | AVS minus VAVS (Avg) | Anti-Tumor (AT) Score (Avg) | (AVS − VAVS)/AT Ratio (Avg) |
|---|---|---|---|---|---|---|---|
| Bevacizumab 2.5 mg/ml | 51 | 24.7 | 5 | <0.0001 | 19.7 | 12.9 | 1.53 |
| DMSO 0.5% + EtOH 0.5% | 40 | 12.7 | 3.5 | <0.0001 | 9.2 | 3 | 3.67 |
| Bevacizumab + DMSO/EtOH | 37 | 32.8 | 11.5 | <0.0001 | 21.3 | Not scored | N/A |
| Cisplatin 3.3 µg/ml | 37 | 4.5 | 3.9 | 0.37 | 0.6 | 59.2 | 0.01 |
| Sunitinib 8.35 µg/ml | 26 | 9.5 | 4.6 | 0.082 | 4.9 | 25.8 | 0.19 |
| Gefitinib 22.35 µg/ml | 32 | 8.3 | 3.8 | 0.0002 | 4.5 | 28.5 | 0.16 |
| Erlotinib 89.4 µg/ml | 45 | 16.2 | 12 | 0.0014 | 4.2 | 22.5 | 0.19 |
| Sorafenib 12.5 µg/ml | 35 | 12.2 | 10.8 | 0.24 | 1.4 | 28.7 | 0.05 |
| Imatinib 12.5 µg/ml | 36 | 13.9 | 11.1 | 0.03 | 2.8 | 23.6 | 0.12 |

Figure 2:
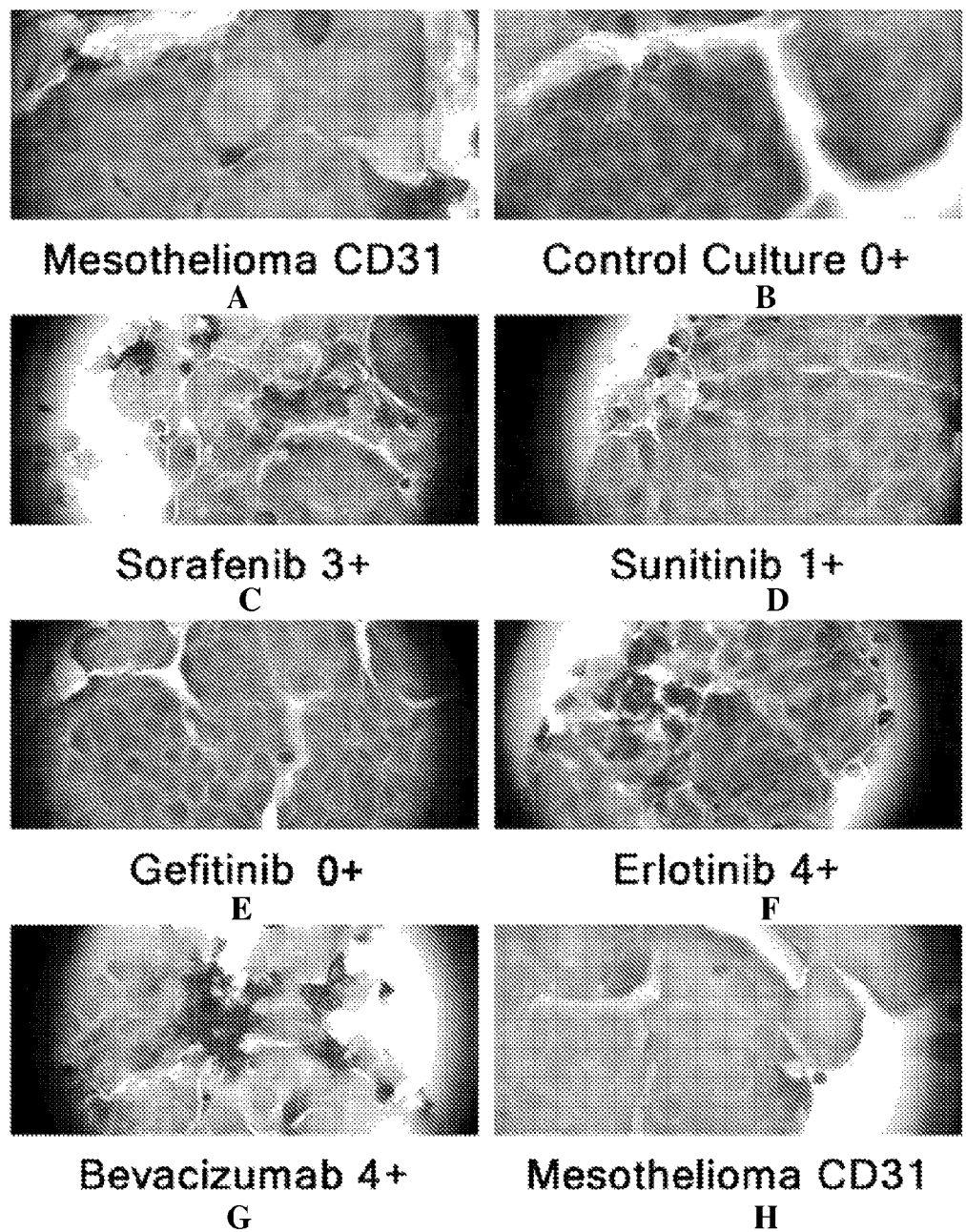
FIGS. 2A-2H show the ability of various kinase inhibitor drugs to exert an antiangiogenic effect as compared to bevacizumab.

The scores provided in FIG. 2 were multiplied by 10 and averaged to give an anti-vascular score (AVS) shown in column 2; the average AVS for the vehicle alone (VAVS) is shown in column 3 and the level of the statistical significance of their difference is shown in column 4. The AVS score was corrected for the effect of vehicle by subtraction as shown in column 5. The antitumor score (AT) is shown in column 6.

Finally, the ratio of AVS (corrected for the effect of vehicle) to the antitumor score is shown in the last column.

As will be apparent from reference to the Table, bevacizumab has a relatively high ratio as compared to the other drugs. It is also apparent that the DMSO/EtOH combination (as compared to 0.9% NaCl) itself has a significant anti-microvasculature effect.

EXAMPLE 3

Synergistic Effects of Combinations

Figure 3:
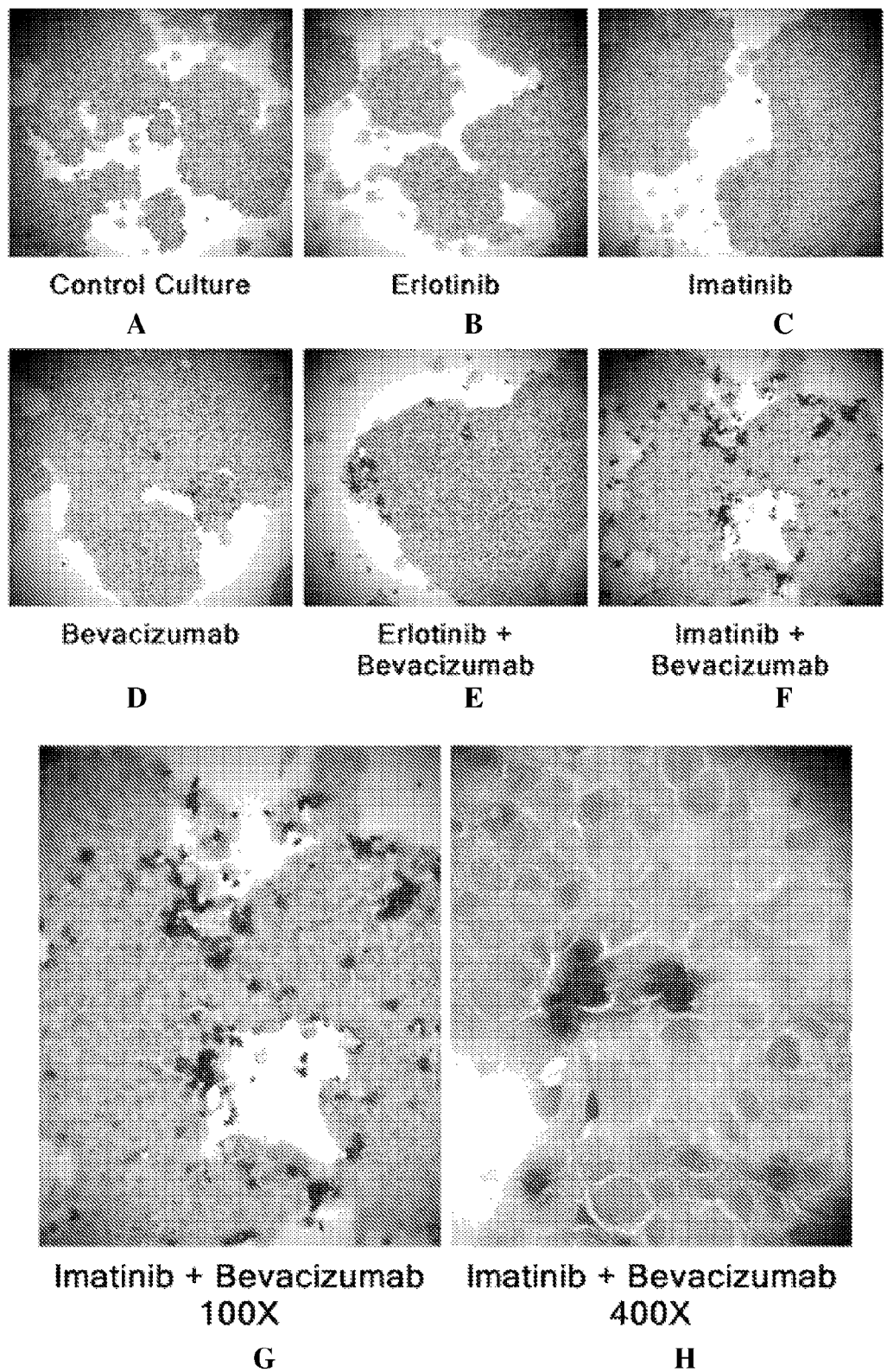
FIGS. 3A-3H show the ability of combinations of bevacizumab with kinase inhibiting drugs to effect endothelial cell killing.

A specimen of poorly differentiated breast cancer was used in the procedures set forth in the previous examples and tested with various drugs and drug combinations as described above. FIGS. 3A-3H show the results. FIG. 3A shows the appearance after staining with Fast Green/H&E on a control culture. FIGS. 3B, 3C and 3D show the appearance when treated with erlotinib, imatinib and bevacizumab alone. None appeared particularly effective, although bevacizumab was scored as +1. Combinations of bevacizumab with either erlotinib (FIG. 3E) or imatinib (FIG. 3F) showed much better results. FIGS. 3G and 3H are simply greater magnifications of the results shown in FIG. 3F.

EXAMPLE 4

Application to Peripheral Blood

Figure 4:
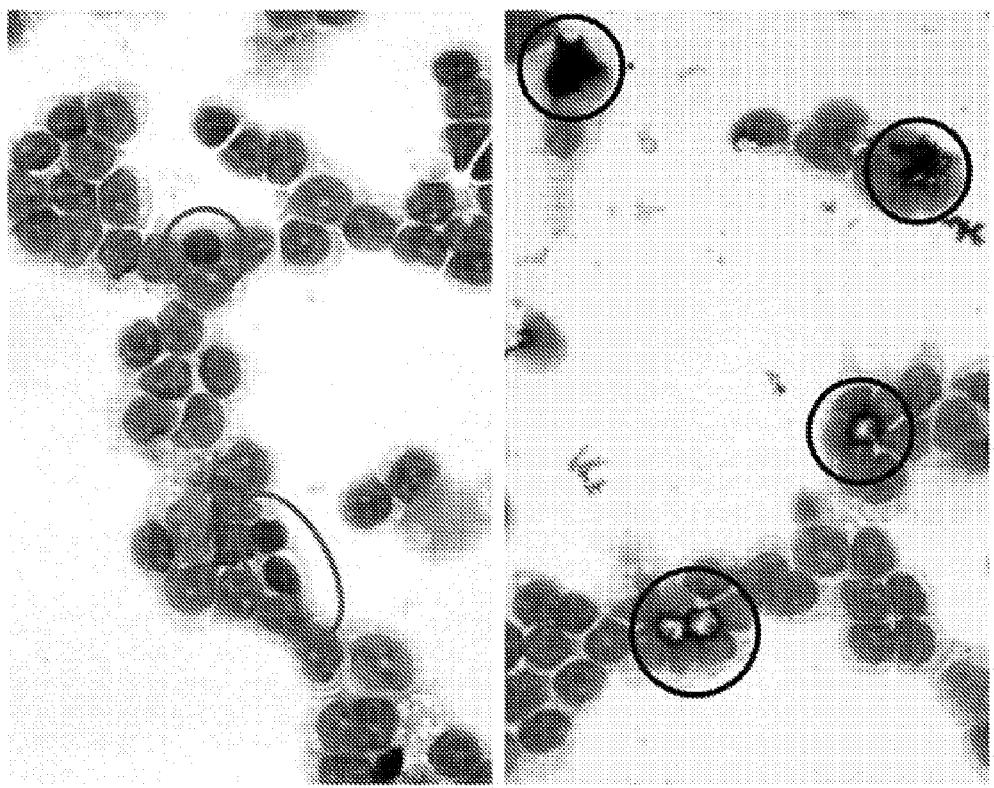
FIGS. 4A and 4B show the combined effects of imatinib and bevacizumab on endothelial cell killing as determined on a sample containing peripheral blood cells.

Peripheral blood chronic lymphocytic leukemia cells were cultured for 4 days in the absence and presence of bevacizumab (2.5 mg/ml) and stained and counterstained as described above. The results are shown in FIG. 4. FIG. 4A shows the culture without bevacizumab. While endothelial cells can be seen, they are clearly less visible than in FIG. 4B where the bevacizumab has caused endothelial cell death. They are readily apparent as refractile, angular small cells of smaller dimension than the surrounding cells. These cells are about one-third the size of lymphocytes and are about 3µ in diameter.

EXAMPLE 5

Quantification of Cell Count

Figure 5:
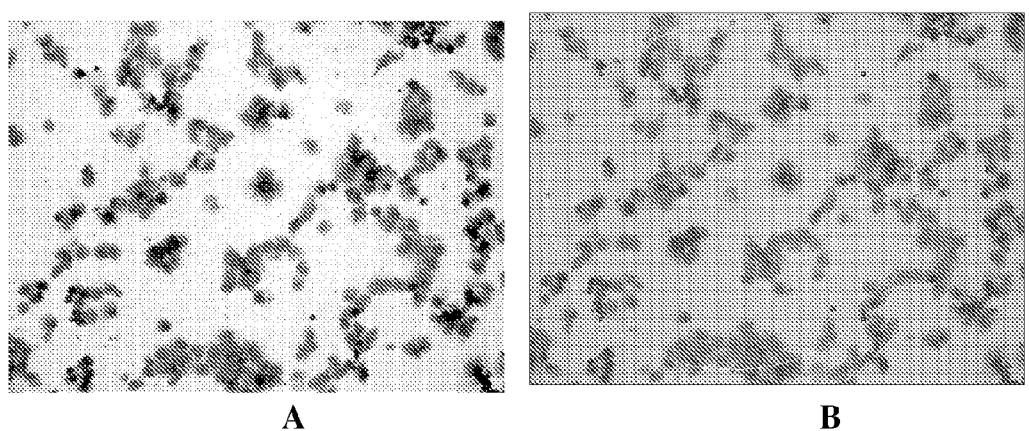
FIGS. 5A and 5B show images used to quantify endothelial cells in a sample.

A lymph node biopsy was obtained from a non-Hodgkin's Lymphoma patient and processed and stained as described above. FIG. 5A is a 200× view of cells cultured 4 days with bevacizumab. The presence of dead endothelial cells is readily apparent. The cells can also be imaged using publicly available "ImageJ" software available from the National Institutes of Health (NIH) to assist quantitation. The image is converted to 8-bit black and white threshold gated to paint only the dead endothelial cells. Only the painted features were counted and measured by software and the resulting image is shown in FIG. 5B.

Figure 6:
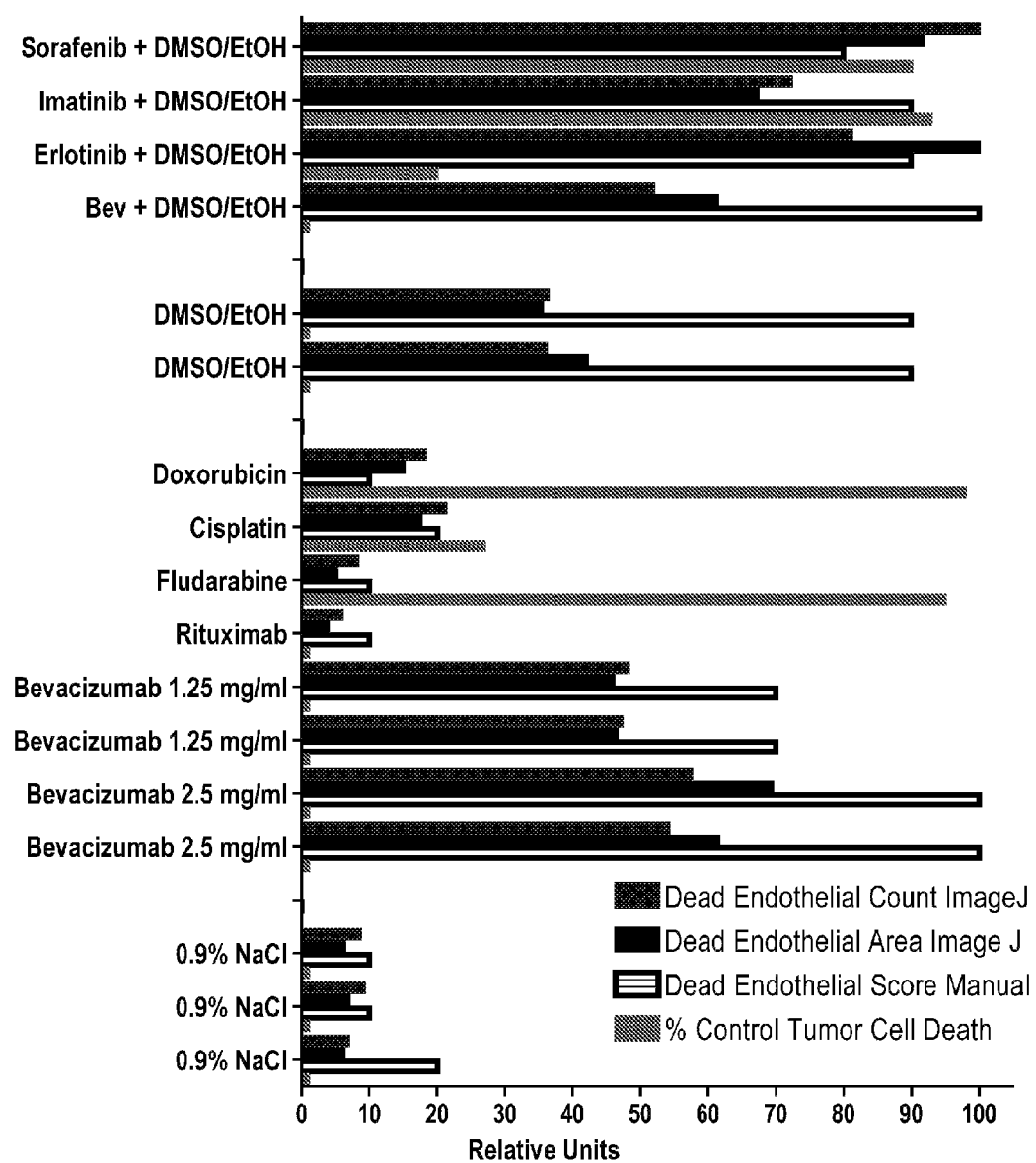
FIG. 6 is a graph showing effects of various drugs on endothelial and non-Hodgkin's Lymphoma (NHL) cells.

The same sample was tested against various drug and vehicle combinations with the results shown in FIG. 6.

The objective, automated ImageJ scores for both individual gated features and also for total area (originally in pixels squared) is shown. The raw scores for the gated features (putative dead endothelial cells) are normalized for uneven cell distributions by image analyzing each area twice: first with the detection threshold set to gate only the features of interest (putative dead endothelial cells) and then again to detect all features on the slide (this would be analogous to normalizing gene copy to total DNA in cell extracts). Shown additionally are the subjective (0+ to 5+) manual anti-vascular scores which were obtained one month before the installed the ImageJ software was installed. Shown additionally are the direct antitumor cell effects of each of the drugs and solvents tested.

As shown, 0.9% NaCl as a vehicle had essentially no antitumor or anti-microvascular activity. However, DMSO/EtOH had significant anti-microvascular activity but no direct antitumor activity. In this particular sample, doxorubicin and fludarabine had direct antitumor effects but were relatively ineffective as anti-microvascular agents. Bevacizumab had essentially no direct antitumor effects as expected, while sorafenib, imatinib, and to a lesser extent, erlotinib acted directly on tumor cells. Their anti-microvascular effects appear comparable to those of vehicle alone.

Figure 7:
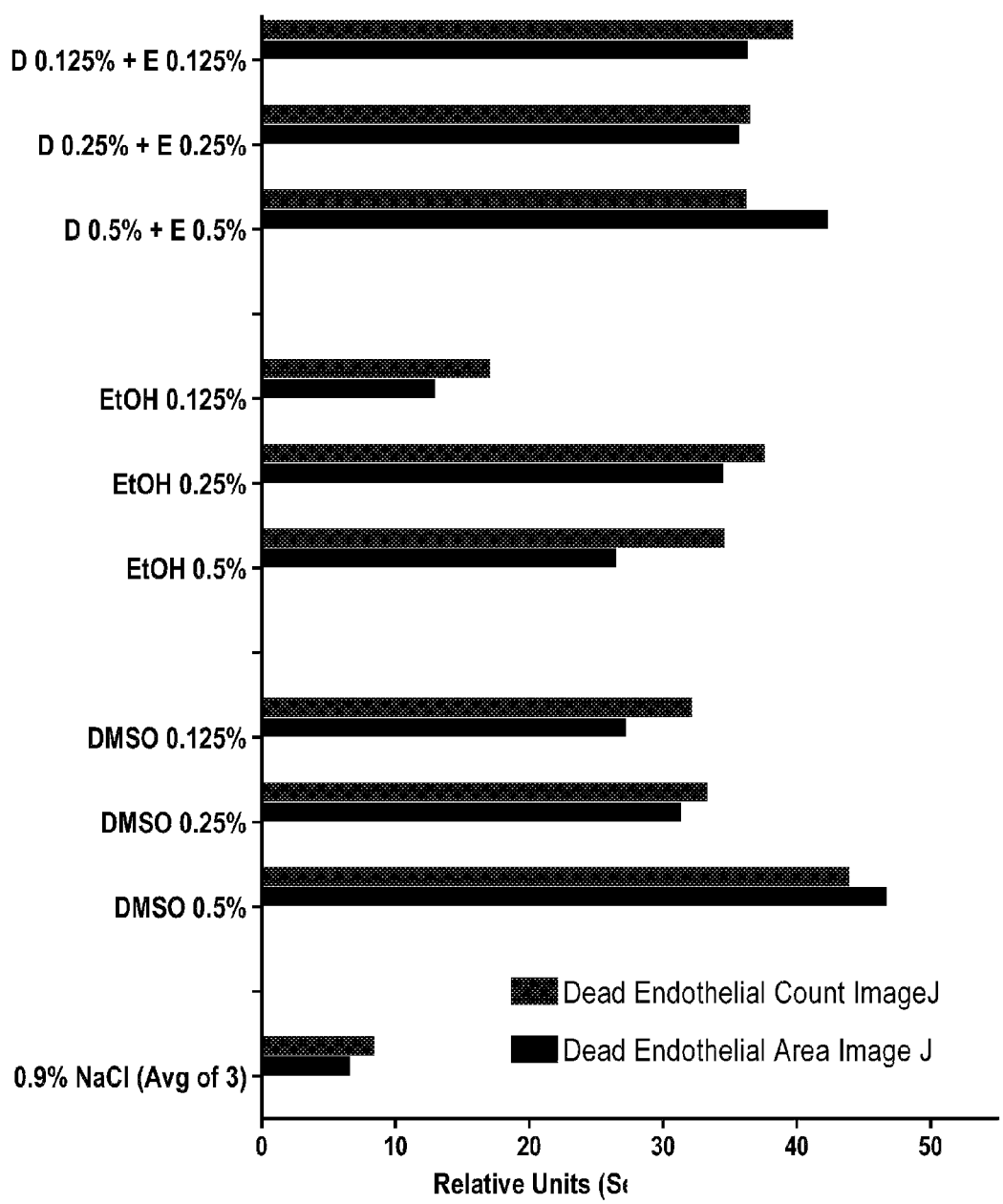
FIG. 7 is a graph showing the anti-angiogenic cell effects of ethanol and DMSO.

The effects of ethanol and DMSO were further confirmed as shown in FIG. 7 using the same sample. These effects were achievable even at relatively low dosage concentrations of 0.125% of the final medium.

EXAMPLE 6

Clinical Illustration of the Effect of Blood Alcohol

A patient at the University of Pennsylvania afflicted with adenocarcinoma of the lung which was metastatic to the brain had been heavily pretreated with chemotherapy, and brain radiation therapy without significant affects. Subsequently, he was treated with Avastin® (bevacizumab) and Tarceva® (erlotinib) along with 4 days of drinking red wine with a breathalyzer so as to keep the blood alcohol above 0.1%. A subsequent MRI of his brain showed regression of multiple brain tumors.

EXAMPLE 7

Detection of Endothelial Cells in the Presence of Lymphatic Cells Obtained from Multiple Subjects Lymph samples from five lymphoma patients and two normal volunteers were cultured and stained as described above. In each case, cultures were treated or not treated with bevacizumab in order to assess the effect of endothelial cell death on visibility and ease of detection. The quantitation of results was as described in Example 4 using ImageJ software. The results are shown in Table 2.

TABLE 2

| Diagnosis | Visualization Reagent | Relative Image J Feature Count | Relative Image J Feature Area |
| --- | --- | --- | --- |
| NHL Patient 1 | 0.9% NaCl | 0.32 | 0.17 |
| NHL Patient 1 | Bevacizumab | 16 | 23 |
| NHL Patient 2 | 0.9% NaCl | 0 | 0 |
| NHL Patient 2 | Bevacizumab | 7.8 | 9.3 |
| NHL Patient 3 | 0.9% NaCl | 8.3 | 6.5 |
| NHL Patient 3 | Bevacizumab | 54 | 61 |
| CLL Patient 4 | 0.9% NaCl | 0.84 | 0.61 |
| CLL Patient 4 | Bevacizumab | 21 | 34 |
| ALL Patient 5 | 0.9% NaCl | 3.7 | 4.4 |
| ALL Patient 5 | Bevacizumab | 39 | 50 |
| Normal Volunteer 6 | 0.9% NaCl | 0.61 | 0.26 |
| Normal Volunteer 6 | Bevacizumab | 3.7 | 1.4 |
| Normal Volunteer 7 | 0.9% NaCl | 2.1 | 0.8 |
| Normal Volunteer 7 | Bevacizumab | 52 | 32 |

As Table 2 shows, the visibility of endothelial cells was greatly enhanced in all of the lymphoma patients by the addition of bevacizumab. Normal Volunteer 6 had only a small number of endothelial cells in the sample, while Normal Volunteer 7 had high levels. This implies that Volunteer 6 is free of conditions associated with sloughed endothelial cells where Volunteer 7 is not.

EXAMPLE 8

Effect of EtOH/DMSO on Levels of Vascular Endothelial Growth Factor (VEGF) in Cell Cultures The observed ability of EtOH/DMSO to effect killing of microvascular/endothelial cells may be due to the ability of these solvents to reduce the levels of VEGF in cell culture. It is known that tumor cells secrete VEGF and VEGF is needed, for the growth of neovasculature. Accordingly, a number of tumor cell cultures were treated with these solvents. The level of VEGF in the cultures was measured by subtracting the optical density at 570 nm from the optical density of 450 nm. The results are drawn in Table 3.

TABLE 3

| Contents of culture well | 450-570 O.D. #1 | 450-570 O.D. #2 | 450-570 O.D. #3 |
| --- | --- | --- | --- |
| Std 0 pg/ml | 0.058 | | |
| Std 15.6 | 0.086 | | |
| Std 31.2 | 0.122 | | |
| Std 62.5 | 0.235 | | |
| Std 125 | 0.305 | | |
| Std 250 | 0.656 | | |
| Std 500 | 1.300 | | |
| Std 1000 | 2.180 | | |
| No cells/RPMI + Serum | 0.055 | 0.057 | 0.058 |
| No cells/RPMI/No Serum | 0.055 | 0.055 | 0.056 |
| No cells/0.9% NaCl | 0.056 | | |
| Pt 1 Cells (P1C; Merkel Tumor, 10% DMSO Cryopreserved) | 0.075 | 0.089 | 0.079 |
| P1C + Bev 2.5 mg/ml | 0.051 | 0.052 | 0.054 |
| P1C + Bev 1.25 mg/ml | 0.054 | 0.054 | 0.059 |
| P1C + EtOH 0.5% + DMSO 0.5% | 0.055 | 0.055 | 0.054 |
| P1C + Cisplatin/Anguidine | 0.058 | 0.062 | |
| Pt 2 Cells (P2C; Ovarian, 10% DMSO Cryopreserved) | 0.065 | 0.079 | 0.082 |
| P2C + Bev 2.5 mg/ml | 0.052 | 0.056 | 0.054 |
| P2C + Bev 1.25 mg/ml | 0.059 | 0.055 | 0.054 |
| P2C + EtOH 0.5% + DMSO 0.5% | 0.054 | 0.054 | 0.055 |
| P2C + Cisplatin/Anguidine | 0.055 | 0.057 | |
| Pt 3 Cells (P3C; Breast; Fresh) | >3.4 | 3.34 | >3.4 |
| P3C + Bev 2.5 mg/ml | 0.056 | 0.059 | |
| P3C + Bev 1.25 mg/ml | | | |
| P3C + EtOH 0.5% + DMSO 0.5% | | | |
| P3C + Cisplatin/Anguidine | 0.284 | 0.308 | |

TABLE 3-continued

| Contents of culture well | 450-570 O.D. #1 | 450-570 O.D. #2 | 450-570 O.D. #3 |
|---|---|---|---|
| Pt 4 Cells (P4C; NHL, Fresh) | 0.051 | 0.051 | 0.052 |
| P4C + Bev 2.5 mg/ml | 0.055 | 0.055 | |
| P4C + Bev 1.25 mg/ml | 0.074 | 0.068 | |
| P4C + EtOH 0.5% + DMSO 0.5% | 0.057 | 0.052 | |
| P4C + Cisplatin/Anguidine | 0.053 | 0.051 | |
| Pt 5 Cells (P5C; Breast, Fresh) | 1.005 | 1.895 | 1.09 |
| P5C + Bev 2.5 mg/ml | 0.053 | | |
| P5C + Bev 1.25 mg/ml | | | |
| P5C + EtOH 0.5% + DMSO 0.5% | | | |
| P5C + Cisplatin/Anguidine | | | |
| Pt 6 Cells (PC; Breast, Fresh) | 2.3 | >3.4 | |
| P6C + Bev 2.5 mg/ml | 0.052 | | |
| P6C + Bev 1.25 mg/ml | 0.063 | | |
| P6C + EtOH 0.5% + DMSO 0.5% | 0.064 | 0.097 | |
| P6C + Cisplatin/Anguidine | 0.098 | 0.187 | |

Table 3 shows the standard curve for 0-1,000 pg/ml of VEGF with a reading of 0.058 for 0 concentration and 2.180 for 1,000 pg/ml. The table also shows that samples of medium, medium plus serum, and 0.9% NaCl show 0 VEGF concentration. For tumor samples preserved in 10% DMSO, only very low levels of VEGF were observed. For fresh breast tumor cells, the levels of VEGF were off-scale, but could be brought to 0 using bevacizumab as expected. Of particular interest are the cells from Patient 6, shown at the end of the table. Fresh breast tumor cells showed values of VEGF that were very high. The combination of 0.5% EtOH and 0.5% DMSO was able to reduce these levels almost to zero.

The invention claimed is:

1. A method to detect and optionally quantify circulating endothelial cells in a vertebrate subject which method comprises
    (a) contacting body fluid that contains circulating cells obtained from said subject with an antiangiogenic agent so as to render living endothelial cells nonviable;
    (b) treating the cells with a dye that is excluded by viable cells but taken up by dead cells; and
    (c) observing the resulting cells under a microscope, and
    (d) identifying the nonviable endothelial cells in said fluid by their dye-staining, size of about one third that of lymphocytes, angular appearance and intense and refractile color,
    wherein the body fluid is blood, lymph or plasma.

2. The method of claim 1 wherein the dye is Fast Green.

3. The method of claim 1 wherein the cells are further treated with a dye that stains viable cells.

4. The method of claim 3 wherein said dye that stains viable cells is hematoxylin/eosin (H&E) or Wright-Giemsa.

5. The method of claim 1 which further comprises quantifying the endothelial cells.

6. The method of claim 1 wherein the body fluid is blood or plasma.

7. A method to assess the effectiveness of a therapeutic agent which method comprises comparing the level of circulating endothelial cells in the blood, lymph or plasma of a test subject treated with said agent with either
    (i) the level of circulating endothelial cells in the blood, lymph or plasma of said subject prior to treating said agent; or
    (ii) the level of circulating endothelial cells in the blood, lymph or plasma of a control subject not treated with said agent;
    whereby a decreased level of circulating endothelial cells in the blood, lymph or plasma of said test subject as compared to that in the blood, lymph or plasma of the subject of subparagraphs (i) or (ii) is indicative of effectiveness of said agent, and wherein said assessment is conducted by the method of claim 1.

8. A method to detect and optionally quantify endothelial cells in a tissue which method comprises
    (a) disaggregating said tissue to obtain a sample that includes any endothelial cells contained therein,
    (b) treating the sample with an antiangiogenic agent to render living endothelial cells nonviable;
    (c) treating the sample with a dye that is excluded by viable cells but taken up by dead cells; and
    (d) observing the cells in the sample under a microscope, and
    (e) identifying the nonviable endothelial cells in said sample by their dye-staining, size of about one third that of lymphocytes, angular appearance and intense and refractile color.

9. The method of claim 8 wherein said antiangiogenic agent is bevacizumab.

10. The method of claim 8 wherein the dye is Fast Green.

11. The method of claim 8 wherein the cells are further treated with a dye that stains viable cells.

12. The method of claim 11 wherein said dye that stains viable cells is hematoxylin/eosin (H&E) or Wright-Giemsa.

13. The method of claim 8 which further comprises quantifying the endothelial cells.

14. A method to determine the effect of a treatment on viability of endothelial cells in a tissue, which method compromises
    (a) contacting said tissue comprised of at least viable endothelial cells and natively surrounding viable non-endothelial cells with said treatment to be tested for its effect on endothelial cell viability, (b) if necessary, disaggregating the tissue to obtain a sample containing any endothelial cells without effecting any additional endothelial cell death,
(c) treating the sample with a dye that is excluded by viable cells but taken up by dead cells;
(d) observing the resulting cells under a microscope, and
(e) identifying the nonviable endothelial cells in said sample by their dye-staining, size of about one third that of lymphocytes, angular appearance and intense and refractile color.

15. The method of claim 14 wherein the dye is Fast Green.

16. The method of claim 14 wherein the cells are further treated with a dye that stains viable cells.

17. The method of claim 16 wherein said dye that stains viable cells is hematoxylin/eosin (H&E) or Wright-Giemsa.